United States Patent
Awbrey

(10) Patent No.: US 8,399,394 B2
(45) Date of Patent: Mar. 19, 2013

(54) SYSTEMS AND METHODS FOR PROCESSING GLYCEROL

(75) Inventor: Spencer S. Awbrey, Conroe, TX (US)

(73) Assignee: Envirosource, Inc., Liberty, TX (US)

( * ) Notice: Subject to any disclaimer, the term of this patent is extended or adjusted under 35 U.S.C. 154(b) by 0 days.

(21) Appl. No.: 13/342,827

(22) Filed: Jan. 3, 2012

(65) Prior Publication Data

US 2012/0129733 A1    May 24, 2012

Related U.S. Application Data

(63) Continuation of application No. 12/965,521, filed on Dec. 10, 2010, now Pat. No. 8,088,948.

(60) Provisional application No. 61/285,890, filed on Dec. 11, 2009.

(51) Int. Cl.
  *C11D 1/04* (2006.01)

(52) U.S. Cl. ........ 510/238; 510/362; 507/267; 252/180; 134/3

(58) Field of Classification Search .................. 510/238, 510/362, 363; 134/3; 507/267; 252/180
See application file for complete search history.

(56) References Cited

U.S. PATENT DOCUMENTS

| | | | |
|---|---|---|---|
| 2,391,462 A | 12/1945 | Julian et al. | |
| 3,639,278 A | 2/1972 | Haw | |
| 3,639,279 A | 2/1972 | Gardner et al. | |
| 3,696,040 A | 10/1972 | Mayo | |
| 4,215,000 A * | 7/1980 | De Jong et al. | 507/241 |
| 4,357,254 A | 11/1982 | Kapiloff et al. | |
| 4,382,035 A | 5/1983 | Eibl | |
| 4,388,203 A | 6/1983 | Nimerick et al. | |
| 5,190,656 A * | 3/1993 | Paul et al. | 210/643 |
| 5,247,992 A | 9/1993 | Lockhart | |
| 5,274,187 A | 12/1993 | Kimura et al. | |
| 5,514,820 A | 5/1996 | Assmann et al. | |
| 5,747,635 A * | 5/1998 | Kroner et al. | 528/328 |
| 6,105,691 A | 8/2000 | Hayatdavoudi et al. | |
| 6,781,020 B2 | 8/2004 | Shiba et al. | |
| 7,270,768 B2 | 9/2007 | Sapienza et al. | |
| 7,388,034 B1 | 6/2008 | Goetsch et al. | |
| 7,696,393 B2 | 4/2010 | Rivers et al. | |
| 2005/0126599 A1 | 6/2005 | Labib et al. | |
| 2005/0215447 A1* | 9/2005 | Evers et al. | 510/238 |
| 2006/0194700 A1* | 8/2006 | Gatlin et al. | 507/140 |

(Continued)

FOREIGN PATENT DOCUMENTS

| | | |
|---|---|---|
| FR | 1598737 | 7/1970 |
| WO | 8202379 | 7/1982 |

OTHER PUBLICATIONS

Ooi T L, et al. Crude Glycerine Recovery From Glycerol Residue Waste From a Palm Kernel Oil Methyl Ester Plant, Journal of Oil Palm Research, Dec. 2001, p. 16-22, vol. 13 No. 2, Malaysian Palm Oil Board, Kuala Lumpur, Malaysia.

(Continued)

*Primary Examiner* — Gregory Webb
(74) *Attorney, Agent, or Firm* — Edmonds & Nolte, P.C.

(57) ABSTRACT

Systems and methods for processing glycerol into one or more useful products are provided. The method can include decreasing a pH of a mixture comprising glycerol and fatty acids to produce an emulsion comprising a glycerol-rich portion and a fatty acids-rich portion. At least a portion of the glycerol-rich portion can be reacted with at least one of an oxidant and a catalyst at conditions sufficient to produce a reacted product comprising glyceric acid, oxalic acid, glycolic acid, formic acid, or any combination thereof.

20 Claims, 1 Drawing Sheet

U.S. PATENT DOCUMENTS

| | | | |
|---|---|---|---|
| 2006/0276366 A1* | 12/2006 | Deljosevic et al. | 510/302 |
| 2006/0287209 A1* | 12/2006 | Chaigne et al. | 510/238 |
| 2007/0151146 A1 | 7/2007 | Lee et al. | |
| 2008/0039345 A1* | 2/2008 | Kippie et al. | 507/119 |
| 2008/0039347 A1* | 2/2008 | Welton et al. | 507/213 |
| 2008/0092438 A1 | 4/2008 | Gaus et al. | |
| 2008/0139412 A1* | 6/2008 | Fuller | 507/219 |
| 2009/0054701 A1 | 2/2009 | Abhari | |
| 2009/0075846 A1 | 3/2009 | Qu et al. | |
| 2009/0149683 A1 | 6/2009 | Awbrey et al. | |
| 2009/0178928 A1 | 7/2009 | Groos et al. | |
| 2009/0197786 A1* | 8/2009 | Perry et al. | 510/191 |
| 2009/0198048 A1 | 8/2009 | Winowiski et al. | |
| 2009/0198088 A1 | 8/2009 | Tirio et al. | |
| 2009/0261290 A1 | 10/2009 | Sapienza et al. | |
| 2010/0005708 A1 | 1/2010 | Estevez Company et al. | |
| 2011/0028360 A1* | 2/2011 | Jenkins | 507/256 |
| 2011/0112006 A1* | 5/2011 | Cobb et al. | 510/405 |
| 2011/0160116 A1* | 6/2011 | Mckechnie et al. | 510/362 |

OTHER PUBLICATIONS

Tapasvi, D. et al., Process Model for Biodiesel Production From Various Feedstocks, Journal, 2005, p. 2215-2221, vol. 48(6), American Society of Agricultural Engineers, United States.

Ernest Gutmann—Yves Plasseraud S.A.S., Letter to Mr. Robb D. Edmonds, pp. 1-5, Jul. 21, 2011.

International Search Report and Written Opinion issued in Patent Application No. PCT/US2010/059929, dated Feb. 11, 2011 (11 pages).

International Search Report and Written Opinion issued in Patent Application No. PCT/US2011/030958, dated Apr. 1, 2011 (7 pages).

Luque et al. Applied Catalysis B: Environmental, 2008, 82, 157-162.

Zhou, et al., Chemical Society Reviews, 2008, 37, 527-549.

DuBois, The Journal of Industrial and Engineering Chemistry, 1913, 6(2) 122-128.

* cited by examiner

SYSTEMS AND METHODS FOR PROCESSING GLYCEROL

CROSS REFERENCE TO RELATED APPLICATION

This application is a continuation of co-pending U.S. patent application, having Ser. No. 12/965,521, filed on Dec. 10, 2010, and published as U.S. Publication No. 2011/0140032, which claims the benefit of U.S. Provisional Patent Application having Ser. No. 61/285,890, filed on Dec. 11, 2009, which are both incorporated by reference herein.

BACKGROUND

1. Field

Embodiments described herein generally relate to systems and methods for processing a glycerol-containing feed. More particularly, such embodiments relate to systems and methods for processing a glycerol-containing feed into one or more products.

2. Description of the Related Art

The level of biodiesel production, an alternative fuel source, has increased significantly in recent years. A byproduct derived from the biodiesel manufacturing process is glycerol, often referred to as "waste glycerol," "crude glycerol," or "raw glycerol." For every tonne (metric ton) of biodiesel made from vegetable oil, 100 kg of thick viscous glycerol is produced as a byproduct. Europe alone produces around 6.8 billion liters of biodiesel, which generates around 680,000 tonnes of waste glycerol every year. And the recent and rapid expansion in biodiesel production has resulted in a global oversupply of waste glycerol.

Although some of the waste glycerol is purified for pharmaceutical or food applications, the majority ends up as waste. Waste glycerol is typically incinerated, which is a less than optimal use for a low cost and readily available byproduct.

There is a need, therefore, for new systems and methods for processing glycerol into one or more products.

SUMMARY

Systems and methods for processing glycerol into one or more products are provided. In at least one specific embodiment, the method can include decreasing a pH of a mixture comprising glycerol and fatty acids to produce an emulsion comprising a glycerol-rich portion and a fatty acids-rich portion. At least a portion of the glycerol-rich portion can be reacted with at least one of an oxidant and a catalyst at conditions sufficient to produce a reacted product comprising glyceric acid, oxalic acid, glycolic acid, formic acid, or any combination thereof. In one or more embodiments, the glycerol-rich portion can be recovered prior to reacting with the oxidant.

In at least one other specific embodiment, the method can include decreasing a pH of a biodiesel byproduct comprising fatty acids, glycerol, water, methanol, and one or more inorganic salts to produce an emulsion comprising a glycerol-rich portion and a fatty acids-rich portion. At least a portion of the glycerol-rich portion can be reacted with at least one of an oxidant and a catalyst at conditions sufficient to produce a reacted product comprising glyceric acid, oxalic acid, glycolic acid, formic acid, or any combination thereof. In one or more embodiments, the glycerol-rich portion can be recovered prior to reacting with the oxidant.

In at least one other specific embodiment, the method can include mixing a biodiesel byproduct with a sufficient amount of an acid to produce a mixture having a pH of less than about 5.5, wherein the biodiesel byproduct comprises fatty acids, glycerol, water, methanol, one or more inorganic salts, and solids, and wherein the acid is not a fatty acid. The mixture can be allowed to separate into a glycerol-rich portion and a fatty acids-rich portion. The glycerol-rich portion can be recovered. At least a portion of the recovered glycerol-rich portion can be filtered to remove at least a portion of the solids. At least a portion of the filtered glycerol-rich portion can be reacted with at least one of an oxidant and a catalyst at conditions sufficient to produce a reacted product comprising glyceric acid, oxalic acid, glycolic acid, formic acid, or any combination thereof. The reacted product can be contacted with a fluid. The reacted product can be used to remove inorganic mineral scale deposits, inhibit the formation of inorganic scales, reduce the freeze point of the fluid, remove hydrates, inhibit the formation of hydrates, or any combination thereof.

DETAILED DESCRIPTION

Figure 1:
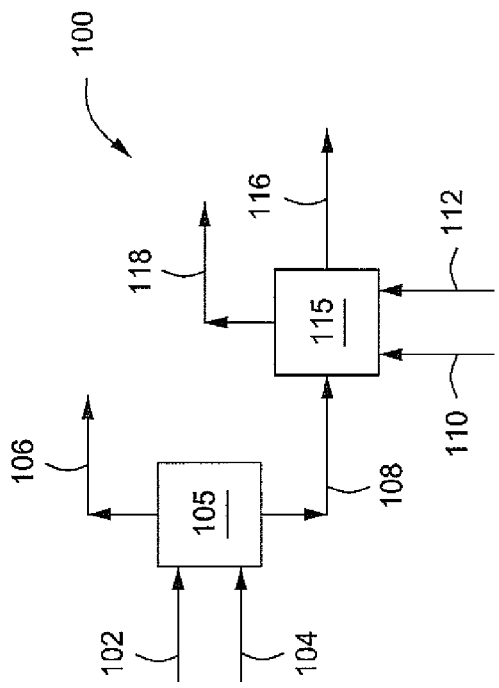
FIG. 1 depicts an illustrative system for processing glycerol, according to one or more embodiments described.

FIG. 1 depicts an illustrative system 100 for processing glycerol, according to one or more embodiments. A glycerol-containing feed via line 102 and an acid via line 104 can be introduced to one or more mixers 105, where the two components can be mixed, blended, or otherwise combined together to produce a mixture. The mixture can be allowed to separate within the mixer 105 into two or more fractions or portions, including a first portion or glycerol-lean portion and a second portion or glycerol-rich portion.

As used herein, the terms "glycerol-lean portion" and "fatty acids-rich portion" are used interchangeably to refer to a mixture or composition that has a greater concentration of fatty acids than glycerol. Similarly, the term "glycerol-rich portion" and "fatty acids-lean portion" are used interchangeably to refer to a mixture or composition that has a greater concentration of glycerol than fatty acids.

The first portion or glycerol-lean portion via line 106 and the second portion or glycerol-rich portion via line 108 can be recovered from the mixer 105. The recovered glycerol-rich portion via line 108 and an oxidant via line 110 can be introduced to one or more reactors 115 to produce a reacted product via line 116 and an off-gas via line 118. One or more catalysts via line 112 can be introduced to the reactor 115 in lieu of or in addition to the oxidant in line 110.

Figure 2:
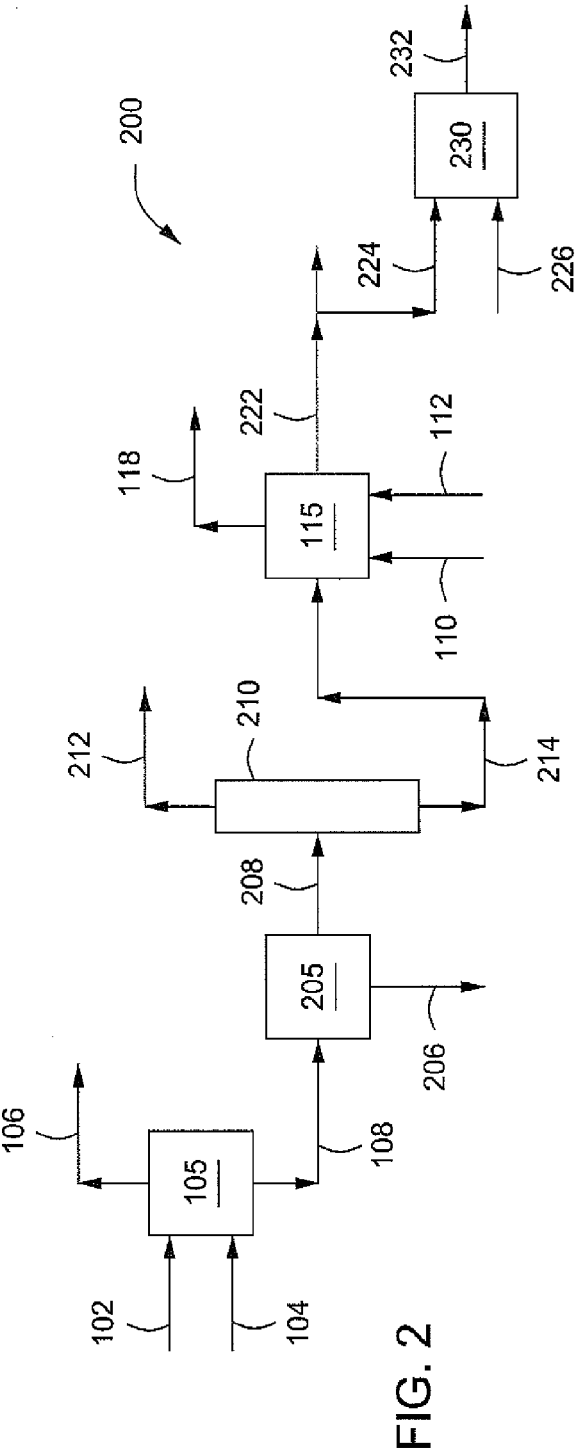
FIG. 2 depicts another illustrative system for processing glycerol, according to one or more embodiments described.

FIG. 2 depicts another illustrative system 200 for processing glycerol, according to one or more embodiments. The system 200 can include the mixer(s) 105 and reactor(s) 115 mentioned above and can further include one or more particulate separation units or filters 205 to remove solids, one or more separators 210 to remove methanol, and one or more additional mixers 230. As discussed above, the glycerol-containing feed via line 102 and the acid via line 104 can be introduced to the one or more mixers 105, where the two components can be mixed, blended, or otherwise combined together to produce a mixture and separated into at least two fractions or portions. A first portion or glycerol-lean portion and a glycerol-rich portion.

If solids are present in the glycerol-rich portion, the glycerol-rich portion via line 108 can be introduced to the one or more particulate separation units or filters 205 to produce a solids-rich product via line 206 and a filtered glycerol-rich portion having a reduced concentration of solids via line 208 relative to the glycerol-rich portion in line 108. The particulate removal unit or filter 205 can be or include any device capable of separating at least a portion of any solids contained in the glycerol-rich portion in line 108. Illustrative filters can include, but are not limited to, rigid or flexible screens, pleated cartridges, melt blown cartridges, woven fabrics, non-woven fabrics, sintered metals, granular media, membranes, centrifugal separators, bag filters, strainers, or any combination thereof. Screens can include wedge-wire screens, weave-wire screens such as square weave, Dutch Weave, and Double Dutch Weave, or any combination thereof. Membranes can include ceramic membranes, polymer membranes, or a combination thereof. The particulate removal unit 205 can separate particles having a size ranging from a low about 0.1 μm, about 0.5 μm, or about 1 μm to a high of about 3 μm, about 5 μm, about 10 μm, for example. The particulate removal unit 205 can remove from about 50% to about 100% of the solids contained in the glycerol-rich portion in line 108. For example, the particulate removal unit 205 can remove about 50%, about 60%, about 70%, about 80%, about 90%, or about 95% of the solids contained in the glycerol-rich portion in line 108.

The filtered glycerol-rich portion via line 208 can be introduced to the one or more separators 210, which can remove or otherwise separate methanol, if present, in the filtered glycerol-rich portion of line 208. The separated methanol can be recovered via line 212 and a glycerol-rich portion having a reduced concentration of methanol can be removed via line 214. The glycerol-rich portion via line 214 and the oxidant via line 110 and/or the catalyst via line 112 can be introduced to the one or more reactors 115 to produce a reacted product ("first product") via line 222 and an off-gas via line 118.

As a result of separating methanol within the separator 210, the concentration of formic acid in the reacted product of line 222 can be reduced relative to the concentration of formic acid in the reacted product of line 116 (FIG. 1) since formic acid is a reaction product from reacting methanol with the oxidant and/or catalyst in reactor 115. Therefore, removing at least a portion of any methanol, if present, in the glycerol-rich portion in line 208 can reduce the concentration of formic acid in the reacted product recovered via line 222 relative to the concentration of formic acid in the reacted product in line 116.

At least a portion of the reacted product of line 222 can be introduced via line 224 to the one or more additional mixers ("second mixer") 230 where a base compound via line 226 can be mixed, blended, or otherwise combined with the product from line 224 to produce a second reacted product via line 232. Combining the reacted product of line 224 with the base compound of line 226 can produce a second reacted product via line 232 having a higher pH (i.e. more alkaline) than the reacted product of line 116 (FIG. 1) and/or 222 (FIG. 2). A product with a pH in the range of about 5.5 to about 8.0 can be useful as a hydrate inhibitor, and can facilitate certain gas recovery, as described in more detail below.

Referring to FIGS. 1 and 2, the glycerol-containing feed in line 102 can include, but is not limited to, glycerol, monoglycerides, diglycerides, methanol, soaps of fatty acids, fatty acids, organic salts, inorganic salts, water, biodiesel, solids, or any combination thereof. The glycerol-containing feed in line 102 can come from any number of sources or processes. For example, the glycerol-containing feed via line 102 can be or include a byproduct from the production of biodiesel. In another example, the glycerol-containing feed can be or include a byproduct from the production of soaps, e.g. produced by the saponification of animal fats. In yet another example, the glycerol-containing feed can include glycerol produced from the conversion of epichlorohydrin. In yet another example, the glycerol-containing feed can be or include a byproduct from the refining of cooking and salad oils. Should the glycerol-containing feed of line 102 be free of fatty acids and soaps of fatty acids, the glycerol-containing feed can bypass the mixer 105 and can be introduced directly to the reactor 115.

Dependent on its source of origin, the glycerol-containing feed in line 102 can have a pH ranging from a low of about 6, about 6.5, or about 7 to a high of about 8, about 9, or about 10, and can include from about 1 wt % to about 99 wt % glycerol. The glycerol-containing feed in line 102 can also include from about 5 wt % to about 15 wt % methanol, from about 5 wt % to about 10 wt % water, from about 20 wt % to about 35 wt % fatty acids and/or soaps of fatty acids, from about 7 wt % to about 15 wt % inorganic and/or organic salts, and/or from about 1 wt % to about 10 wt % solids. The fatty acids can include acyclic and/or aliphatic carboxylic acids. Such fatty acids can contain any where from about 8 to about 22 carbon atoms. With respect to carbon-carbon bonds, the fatty acids can be saturated, monounsaturated, or polyunsaturated. The organic salts can include, but are not limited to, sodium, lithium, salts of fatty acids, proteins, or any combination thereof. The inorganic salts can include, but are not limited to, sodium chloride (NaCl), potassium chloride (KCl), lithium chloride (LiCl), or any combination thereof. The solids can include, but are not limited to, fats, carbons, salts of fatty acids, polymers of fatty acids, or any combination thereof.

The acid in line 104 can be or include any acid or combination of two or more acids. For example, the acid in line 104 can be or include one or more mineral acids, sulfonic acids, carboxylic acids, or any combination thereof. Illustrative mineral acids can include, but are not limited to, hydrochloric acid (HCl), hydrobromic acid (HBr), hydroiodic acid (HI), hypochloric acid, chloric acid, perchloric acid, periodic acid, sulfuric acid ($H_2SO_4$), fluorosulfuric acid ($FSO_3H$), nitric acid ($HNO_3$), phosphoric acid ($H_3PO_4$), fluoroantimonic acid ($HSbF_6$), fluoroboric acid ($HBF_4$), hexafluorophosphoric acid ($HPF_6$), and chromic acid ($H_2CrO_4$). Illustrative sulfonic acids can include, but are not limited to, methanesulfonic acid ($MeSO_3H$), ethanesulfonic acid ($EtSO_3H$), benzenesulfonic acid ($C_6H_5SO_3H$), p-Toluenesulfonic acid ($CH_3C_6H_4SO_3H$), and trifluoromethanesulfonic acid ($CF_3SO_3H$). Illustrative carboxylic acids can include, but are not limited to, acetic acid ($C_2H_4O_2$), citric acid ($C_6H_8O_7$), formic acid ($CH_2O_2$), gluconic acid ($C_6H_{12}O_7$), lactic acid ($C_3H_6O_3$), oxalic acid ($C_2H_2O_4$), and tartaric acid ($C_4H_6O_6$). If the acid in line 104 includes carboxylic acid(s), the number of carbon atoms in the carboxylic acid(s) is preferably less than 8, or less than 7, or less than 6. In at least one specific embodiment, the acid in line 104 can be an acid other than a fatty acid. In at least one specific embodiment, the acid or combination of acids in line 104 is not a carboxylic acid. In at least one specific embodiment, the acid or combination of acids in line 104 is not a fatty acid.

The acid in line 104 can be introduced to the mixer 105 in an amount sufficient to produce a mixture therein having a pH of less than about 5.5, less than about 5, less than about 4.5, or less than about 4. For example, the pH of the mixture can range from a low of about 2.5, about 3, or about 3.5 to a high of about 4, about 4.5, or about 5. The particular amount and/or type of acid added to the mixer 105 can depend, at least in part, on the amount of the glycerol or the fatty acids in the glycerol-containing feed and the pH of the feed. For example, 1 to 100 moles of acid can be added per mole of glycerol-containing feed to meet the desired pH of the resulting mixture. The amount of acid added to the glycerol-containing feed can also range anywhere from about 1:1 to about 90:1; about 5:1 to about 75:1; or about 10:1 to about 20:1, on a volume basis.

The mixer 105 can be any device or system suitable for batch, intermittent, and/or continuous mixing, blending, or otherwise combining of two or more components. For example, the mixer 105 can be any device or system suitable for mixing the glycerol-containing feed in line 102 and the acid in line 104. The mixer 105 can be capable of producing a homogenized mixture. Illustrative mixers can include, but are not limited to, mechanical mixer agitation, ejectors, static mixers, mechanical/power mixers, shear mixers, sonic mixers, or combinations thereof. The mixer 105 can include one or more heating jackets, heating coils, internal heating elements, or the like, to regulate the temperature therein.

Decreasing the pH of the glycerol-containing feed in line 105 by mixing, blending, or otherwise combining the one or more acids of line 104 therewith facilitates the separation of the glycerol from the glycerol-containing feed. The lower pH forms an emulsion of a first layer or "glycerol-lean portion" and a second layer or "glycerol-rich portion." The first layer can also be referred to as a "fatty acids-rich portion," and can include the fatty acids, soaps of fatty acids, and/or biodiesel from the glycerol-containing feed. The glycerol-rich portion can include the glycerol, monoglycerides, diglycerides, methanol, organic salts, inorganic salts, and/or water from the glycerol-containing feed.

In one or more embodiments, the mixture of the glycerol-containing feed and the acid in the mixer 105 can be heated to accelerate the combining and separation process. For example, the mixture can be heated to a temperature of about 40° C., about 50° C., about 55° C., about 60° C., or about 65° C. If methanol is present and it is desirable to maintain methanol in the glycerol-rich portion of line 108, the temperature can be maintained below about 64.7° C., which is the boiling point of methanol. In at least one specific embodiment, the mixture can be heated to a temperature greater than about 65° C., to vaporize the methanol, if present, in the glycerol-containing feed in line 102. As such, if the glycerol-containing feed includes methanol, the methanol can either be recovered as a separate product or the methanol can remain in the glycerol-rich portion recovered via line 108 by regulating the temperature of the mixer 105. Although not shown, methanol can be recovered or separated from the feed 102 prior to the mixer 105 to produce a methanol-lean glycerol-containing feed in line 102.

The glycerol-rich portion in line 108 can have a glycerol concentration ranging from a low of about 30 wt %, about 40 wt %, or about 45 wt % to a high of about 55 wt %, about 60 wt %, about 65 wt %, about 75 wt %, about 85 wt %, or about 95 wt %. The glycerol-rich portion in line 108 can have a methanol concentration ranging from a low of about 1 wt %, about 5 wt %, or about 10 wt % to a high of about 25 wt %, about 30 wt %, or about 35 wt %. The glycerol-rich portion in line 108 can have a water concentration ranging from a low of about 5 wt %, about 10 wt %, or about 12 wt % to a high of about 15 wt %, about 20 wt %, or about 25 wt %. The glycerol-rich portion in line 108 can have a salt concentration ranging from a low of about 0.5 wt %, about 1 wt %, or about 2 wt % to a high of about 5 wt %, about 7 wt %, or about 9 wt %. The glycerol-rich portion in line 108 can have a solids concentration ranging from a low of about 0.5 wt %, about 1 wt %, or about 3 wt % to a high of about 5 wt %, about 10 wt %, or about 15 wt %. The glycerol-rich portion in line 108 can also include residual or trace amounts of monoglycerides, proteins, amino acids, and/or gums, for example. The glycerol-rich portion in line 108 can have a fatty acids concentration of less than about 15 wt %, less than about 10 wt %, less than about 5 wt %, less than about 3 wt %, less than about 1 wt %, or less than about 0.5 wt %.

The oxidant in line 110 can include one or more oxidants including, but not limited to, hydrogen peroxide ($H_2O_2$), oxygen ($O_2$), ozone ($O_3$), oxygen-containing gases, e.g., air, sodium permanganate, potassium permanganate, sodium persulfate, potassium persulfate, magnesium peroxide, calcium peroxide, sodium percarbonate, or any combinations thereof. The amount of oxidant introduced via line 110 to the reactor 115 can vary, but should be sufficient to at least partially oxidize the glycerol-rich portion introduced via line 108. The amount of oxidant can depend, at least in part, on the amount of the glycerol in the reactor 115 and/or the particular composition or make-up of the glycerol in line 108. In one or more embodiments, the amount of the oxidant introduced via line 110 can be based on the number of moles of oxidant per mole of glycerol and can range from a low of about 0.2 mol %, about 0.4 mol %, about 0.5 mol %, or about 0.8 mol % to a high of about 1 mol %, about 1.2 mol %, about 1.5 mol %, or about 2 mol %.

The reactor 115 can be any container or environment suitable for batch, intermittent, and/or continuous contact of the glycerol-rich portion of line 108 with the oxidant of line 110 and/or the catalyst of line 112. In one or more embodiments, the reactor 115 can be an open vessel or a closed vessel. In one or more embodiments, the reactor 115 can include one or more mixing devices such as one or more mechanical/power mixers and/or sonic mixers. In one or more embodiments, the reactor 115 can include a cooling jacket and/or coil for maintaining a temperature of the reaction mixture at a predetermined temperature. The reactor 115 can include one or more nozzles, fluid distribution grids, or other device(s) for introducing the oxidant to the reactor 110.

Within the reactor 115, at least a portion of the glycerol can react with the oxidant at conditions sufficient to produce glyceric acid, oxalic acid, glycolic acid, formic acid, glyceraldehydes, hydroxypyruvic acid, tartronic acid, derivatives thereof, or any combination thereof. In one or more embodiments, at least a portion of the methanol, if present, can react with the oxidant at conditions sufficient to produce formic acid. Suitable conditions include a temperature of about 70° C. or less, about 65° C. or less, about 60° C. or less, or about 55° C. or less. The reaction temperature can also range from a low of about 0° C., 15° C., or 20° C. to a high of about 50° C., 65° C., or 75° C., although higher temperatures are envisaged.

The one or more catalysts via line 112 can be introduced to the reactor 115, in addition to or in lieu of the oxidant via line 110, to produce the reacted product via line 116. Suitable catalysts can include, but are not limited to, platinum, palladium, carbon supported platinum, potassium permanganate, chromium oxide, carbon supported palladium, silicates, aluminophosphates, or any combination thereof. In at least one specific embodiment, hydrogen peroxide via line 110 and/or a catalyst, e.g., ferrous sulfate and/or potassium permanganate, via line 112 can be introduced to the reactor 115.

The composition or make-up of the reacted product in line 116 can widely vary. The amount of oxidant and/or catalyst, residence time, temperature, pressure, and other process variables can influence the particular products and the relative amounts of those particular products produced. For example, increasing the temperature of the reaction mixture can increase the amount of acids, e.g., carboxylic acids, produced in the reactor 115 and contained in the reacted product in line 116. In another example, increasing the amount of oxidant, relative to the amount of the glycerol-rich portion, can increase the amount of acids, e.g., carboxylic acids, produced in the reactor 115 and contained in the reacted product in line 116.

The reacted product in line 116 can have a concentration of glyceric acid ranging from a low of about 1 wt %, about 10 wt %, or about 20 wt % to a high of 50 wt %, about 60 wt %, about 70 wt %, about 80 wt %, or about 100 wt %. The reacted product in line 116 can also have a concentration of oxalic acid ranging from a low of about 0.1 wt %, about 1 wt %, or about 3 wt % to a high of about 5 wt %, about 7 wt %, or about 10 wt %. The reacted product in line 116 can also have a concentration of glycolic acid ranging from a low of about 0.1 wt %, about 0.5 wt %, or about 1 wt % to a high of about 1.5 wt %, about 2 wt %, or about 3 wt %. The reacted product in line 116 can also have a concentration of formic acid ranging from a low of about 1 wt %, about 5 wt %, or about 10 wt % to a high of about 20 wt %, about 30 wt %, or about 40 wt %. The reacted product in line 116 can also have a concentration of glyceraldehydes ranging from a low of about 0.1 wt %, about 0.5 wt %, or about 1 wt % to a high of about 1.5 wt %, about 2 wt %, or about 3 wt %. The reacted product in line 116 can also have a concentration of hydroxypyruvic acid ranging from a low of about 0.1 wt %, about 1 wt %, or about 1.5 wt % to a high of about 3 wt %, about 5 wt %, or about 7 wt %. The reacted product in line 116 can also have a concentration of tartronic acid ranging from a low of about 0.1 wt %, about 0.5 wt %, or about 1 wt % to a high of about 1.5 wt %, about 2 wt %, or about 3 wt %. The reacted product in line 116 can also have a concentration of water ranging from a low of about 1 wt %, about 5 wt %, or about 10 wt % to a high of about 30 wt %, about 40 wt %, or about 50 wt %. The reacted product in line 116 can also have a concentration of solids ranging from a low of about 0.1 wt %, about 0.5 wt %, or about 1 wt % to a high of about 1.5 wt %, about 2 wt %, or about 3 wt %. The reacted product in line 116 can also have a concentration of glycerol ranging from a low of about 0.1 wt %, about 5 wt %, or about 10 wt % to a high of about 20 wt %, about 30 wt %, or about 40 wt %. The reacted product in line 116 can also have a concentration of methanol ranging from a low of about 0.1 wt %, about 1 wt %, or about 3 wt % to a high of about 5 wt %, about 7 wt %, or about 10 wt %.

Considering the separator 210 of FIG. 2 in more detail, the separator 210 can be empty, partially filled, or completely filled with one or more trays and/or packing to improve mass transfer and/or separation of a multi-component fluid. Illustrative trays can include, but are not limited to, perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof.

The packing can increase the effective surface area, which can improve the mass transfer therein. Suitable packing can include, but is not limited to, metals, non-metals, polymers, ceramics, glasses, or any combination thereof. The packing can be structured and/or random. Suitable structured packing can include Raschig rings, Lessing rings, I-rings, saddle rings, Berl saddles, Intalox saddles, Tellerettes, Pall rings, U-rings, or any combination thereof. Illustrative examples of commercially available structured packing can include, but is not limited to FLEXIPAC® and GEMPAK® structured packing as manufactured by the Koch-Glitsch Corporation, corrugated sheets, crimped sheets, gauzes, grids, wire mesh, monolith honeycomb structures, or any combination thereof.

The separator 210 can be used to separate at least a portion of the methanol, if present, in the glycerol-rich portion in line 208 to provide the methanol via line 212 and the glycerol-rich portion via line 214. The separated glycerol-rich portion via line 214 can have a reduced concentration of methanol relative to the glycerol-rich portion in line 208. The separator 210 can include any number of separation processes, for example, evaporation, fractionation, and/or distillation. In one or more embodiments, all or a portion of the methanol contained in the glycerol-rich portion in line 208 can be separated and recovered via line 212. As such, the glycerol-rich portion recovered via line 214 can include less than about 30 wt %, less than about 20 wt %, less than about 10 wt %, less than about 5 wt %, less than about 2 wt %, less than about 1 wt %, less than about 0.5 wt %, or less than about 0.1 wt % methanol.

The base compound of line 226 that is added to mixer(s) 230 can be or include any base or combination of two or more bases. Illustrative bases or base compounds can include, but are not limited to, potassium hydroxide (KOH), sodium hydroxide (NaOH), lithium hydroxide (LiOH), amines, or any combination thereof. Suitable amines can include, but are not limited to, alkanolamines, polyamines, aromatic amines, and any combination thereof. Illustrative alkanolamines can include, but are not limited to, monoethanolamine (MEA), diethanolamine (DEA), triethanolamine (TEA), or any combination thereof. Illustrative aromatic amines can include, but are not limited to, benzyl amine, aniline, ortho toludine, meta toludine, para toludine, n-methyl aniline, N-N'-dimethyl aniline, di- and tri-phenyl amines, 1-naphthylamine, 2-naphthylamine, 4-aminophenol, 3-aminophenol and 2-aminophenol. Illustrative polyamines can include, but are not limited to, diethylenetriamine (DETA), triethylenetetramine (TETA), tetraethylenepentamine (TEPA) 1,3-propanediamine, 1,4-butanediamine, polyamidoamines, and polyethylenimines.

The particular amount of the base compound added can depend, at least in part, on the amount of the particular composition or make-up of the reacted product, i.e. the particular components and the relative amount of those components contained in the reacted product of line 224. In one or more embodiments, the base compound in line 226 can be introduced to the second mixer 230 in an amount sufficient to produce a mixture therein having a pH of about 6 or more, about 6.5 or more, about 7 or more, about 7.5 or more, about 8 or more, about 8.5 or more. For example, the pH of the mixture within the second mixer 230 can range from a low of about 6, about 6.5, or about 7 to a high of about 8, about 8.5, or about 9. In another example, about 1 to about 100 moles of base can be added per mole of reacted product to meet the desired pH of the resulting mixture in line 232. The amount of base added to the reacted product can also range anywhere from about 1:1 to about 90:1, about 5:1 to about 75:1, or about 10:1 to about 20:1, on a volume basis.

The reacted products, i.e. the reacted product in lines 116, 222, and/or the second reacted product in line 232, can have a flash point greater than about 30° C., greater than about 38° C., greater than about 50° C., greater than about 66° C., or greater than about 93° C. and less than about 300° C., less than about 250° C., or less than about 200° C. For example, the reacted products can have a flash point of about 32° C., about 54° C., about 60° C., about 68° C., about 75° C., or about 95° C. The reacted products can have a freezing point of less than about −25° C., less than about −50° C., less than about −60° C., or less than about −65° C.

The reacted products can also have a specific gravity, relative to demineralized water, ranging from a low of about 1.05, about 1.09, or about 1.15 to a high of about 1.3, about 1.4, or about 1.5. For example, the reacted products can have a specific gravity, with respect to demineralized water, of about 1.1, about 1.2, about 1.25, or about 1.3.

The reacted products can also have a pH of less than about 3.5, less than about 3, less than about 2.5, less than about 2, less than about 1.5, or less than about 1. The pH of the reacted products can also range from a low of about 1, about 1.3, about 1.7, or about 2.1 to a high of about 3, about 3.3, about 3.6, or about 3.9.

The reacted products, i.e. the reacted product of lines 116, 222, and/or the second reacted product of line 232, can be mixed or blended with corrosion inhibitors, polymers, salts, scale removers, surfactants, inhibitors, or any combination thereof and can be used in any number of applications. Illustrative corrosion inhibitors can include, but are not limited to, filmers, neutralizers, or a combination thereof. Illustrative polymers can include, but are not limited to, polyols, polyamides, poly celluloses, poly(acrylic acids), or any combination thereof. Illustrative salts can include, but are not limited to, NaCl, KCl, LiCl, trisodium phosphate (TSP), sodium tripolyphosphate or sodium triphosphate (STPP or STP), tripotassium phosphate (TKPP), potassium triphosphate (KTP), or any combination thereof.

In one or more embodiments, the reacted products of lines 116, 222, and/or 232 can act or work as an acid, a sequestrant, a chelant, a dispersing agent, a solvent, or any combination thereof for removing mineral scale deposits (scale). The formation of scales can be caused by a number of factors, which can include, but are not limited Co, pressure drops, temperature fluctuations, changes in pH or ionic strength, and any combinations thereof. The formation or precipitation of scale deposits can occur in, for example, oil production and/or processing equipment, which can be located above and/or below the surface. The formation or precipitation of scale deposits can also occur in subterranean formations, such as an oil and/or gas producing formations. Oil production and processing equipment can include, flow lines, heaters, pumps, valves, pipes, pipelines, risers, drill strings, wellbores, downhole pumps, perforations, fractures, fissures, and the like. Other areas in which scale deposits can be problematic include, but are not limited to, the chemical processing industries, public utilities, and other processes in which mineral-laden water is processed or used, as in heat exchangers, storage vessels, piping, reactors, evaporators, and the like. Commonly encountered scales include, but are not limited to, calcium carbonate ($CaCO_3$), calcium sulfate ($CaSO_4$), barium sulfate ($BaSO_4$); and sodium chloride (NaCl). Other inorganic mineral deposits can include, strontium sulfate ($SrSO_4$), strontium carbonate ($SrCO_3$), iron oxide ($Fe_2O_3$), iron carbonate ($FeCO_3$), iron sulfide (FeS), barium-strontium sulfate ($BaSr(SO_4)_2$), magnesium carbonate ($MgCO_3$), magnesium sulfate ($MgSO_4$), or any combination thereof.

Introducing the reacted products in lines 116, 222, and/or 232 to equipment, formations, and/or other locations where scale deposits form or can potentially form can reduce scale and/or inhibit or prevent the formation of scale. The reacted products, at any desired concentration, can be used to remove scale and/or prevent or reduce the formation of scale. In one or more embodiments, the reacted products in lines 116, 222, and/or 232 can be diluted with water to provide an aqueous solution having a desired concentration.

In one or more embodiments, the reacted products in lines 116, 222, and/or 232 can be used to demulsify an emulsion. The reacted products, for example, can demulsify an emulsion by lowering the pH of the emulsion and/or by increasing the specific gravity of the produced water. The reacted products can be used as produced, diluted, and/or mixed with other ingredients that can improve the demulsification. Illustrative additional ingredients can include, but are not limited to, silicon compounds, glycols, salts, any other water soluble demulsifiers, or any combination thereof.

In one or more embodiments, the reacted products in lines 116, 222, and/or 232 can be used as a frac fluid, drilling fluid, or component thereof for oil and/or gas production. The reacted products in lines 116, 222, and/or 232 can be used neat or mixed or blended with one or more other fluids. An illustrative frac fluid, for example, can include about 5 wt % to about 25 wt % reacted product, about 5 wt % to about 25 wt % formic acid, and about 45 wt % to about 65 wt % water. Illustrative blending agents and/or additives can include, but are not limited to, drilling fluids, steam, corrosion inhibitors, water, acids such as hydrochloric acid, surfactants, polymers such as polyols, polyamides, poly celluloses, poly(acrylic acids), or any combination thereof. For drilling, the reacted product is particularly useful in water-based drilling fluids.

In one or more embodiments, the reacted products in lines 116, 222, and/or 232 can be used as an anti-icing compound. The reacted products can be used neat, diluted with water, and/or or blended with one or more additives. In at least one specific embodiment, the anti-icing compound can be sprayed, injected, or otherwise introduced on or to pipelines, processing equipment, diluents for chemicals, storage tanks, ships, oil rigs, trucks, and storage equipment, for example.

In one or more embodiments, the reacted products in lines 116, 222, and/or 232 can be used as a general purpose cleaner. As a general purpose cleaner, the reacted products can be used neat, diluted with water, and/or blended with one or more additives. Suitable additives can include, but are not limited to, polymers, salts, and/or other treatment chemicals that can expand or enhance one or more functional properties of the reacted products. In at least one specific embodiment, the reacted products can be diluted with water to provide a cleaning solution having a concentration of the reacted product ranging from about 100 ppmw to about 40 wt %.

In one or more embodiments, the reacted products in lines 116, 222, and/or 232 can be used to prevent or reduce the formation of hydrates in a fluid containing one or more hydrate-forming constituents by contacting the fluid with the reacted product(s). For example, the second reacted product via line 232 can be introduced to a fluid or system that contains hydrates or in which hydrates can potentially form, e.g., a hydrocarbon gas stream containing methane and/or natural gas. Illustrative systems can include, but are not limited to, hydrocarbon production/processing equipment, pipelines, storage tanks, and the like. In at least one specific embodiment, the reacted products can be introduced into a downhole location such as a hydrocarbon production well to control hydrate formation in fluids produced therefrom. In another example, the reacted products can be introduced to a produced hydrocarbon at a wellhead location or into a riser through which produced hydrocarbons are transported in offshore operations from the ocean floor to an offshore production facility. In still another example, the reacted products can be introduced to a hydrocarbon prior to transporting the hydrocarbon, for example, via a subsea pipeline from an offshore production facility to an onshore gathering and/or processing facility. In one or more embodiments, the reacted products can be introduced to a downhole location as a drilling fluid or as a component of a drilling fluid.

In one or more embodiments, the reacted products in lines 116, 222, and/or 232 can be used to recover a gas that is bound or entrained in a formed hydrate. In at least one specific embodiment, the second reacted product via line 232 can be introduced into a downhole location or any other location that contains or may contain hydrates where the second reacted product can release at least a portion of any gases bound or contained in the hydrate(s) present therein. The released gases bound in the hydrate(s) can be recovered as a product.

A mixture that can potentially form or contain hydrates can include, for example a water and gas mixture. The gas can be a hydrocarbon normally gaseous at 25° C. and 100 kPa, such as an alkane of 1-4 carbon atoms, e.g., methane, ethane, propane, n-butane, isobutane, or an alkene of 2-4 carbon atoms, e.g., ethylene, propylene, n-butene, isobutene, or any combination thereof. The gas can include about 80 wt %, about 90 wt %, or more methane. The gas can also include about 0.1 wt % to about 10 wt % $C_2$ hydrocarbons and about 0.01 wt % to about 10 wt % $C_3$ hydrocarbons.

EXAMPLES

In order to provide a better understanding of the foregoing discussion, the following non-limiting examples are offered. Although the examples may be directed to specific embodiments, they are not to be viewed as limiting the invention in any specific respect. All parts, proportions, and percentages are by weight unless otherwise indicated.

Example I

In Example I, an existing well (Well A) that could be produced twice a day for an hour (on pump) for a total of about 4 to about 6 bbls of fluid per day before pumping off was evaluated. A produced water from a different well/different zone was introduced into Well A. The result was an immense calcium carbonate problem. The well had to be completely shut down due to calcium carbonate scaling within the production line as well as near the wellbore and within the formation. More water was attempted to be introduced/forced into the formation in an attempt to open the formation. The well was pressured up to about 4,500 psi but no more water flowed into the formation.

A three hundred (300) gallon "pill" of a reacted product was introduced into the Well A. The reacted product or pill was prepared according to the following process: a biodiesel waste product was mixed with a sufficient amount of hydrochloric acid (HCl) to adjust the pH to about 3 at room temperature and pressure. The mixture was allowed to separate into a glycerol-rich portion and a fatty acids-rich portion. The fatty acids-rich portion was then separated from the glycerol-rich portion. A 30 wt % hydrogen peroxide solution was then added to and reacted with the glycerol-rich portion to produce the reacted product. The amount of hydrogen peroxide added to the glycerol-rich portion was about 10 wt %, based on the total weight of the glycerol-rich portion. From the reacted product, the three hundred gallon pill was acquired.

The three hundred gallon pill was then introduced into Well A via a pump truck. After introduction of the pill, Well A wns pressured up to about 1,750 psi and then shut in. After about 1.5 hours, the pressure on Well A was about 0 psi. Well A was left shut in for about 48 hours, after which time Well A was brought back on line. After bringing Well A back on line, about 65+ bbls of total fluid/day were produced with no stoppage. The oil production fluctuated between about 15 bbls per day and about 25 bbls per day.

Example II

In Example II, a second well (Well B) was producing about 65 bbls per day and had a bottom hole temperature of about 130° F. to about 150° F. The well was treated with another produced water, similar to Example I above, i.e. produced water from another well/zone, and production from the well dropped to about 0.4 bbls of total fluid per day. Well B could only be pumped for about 5 hours before pumping off.

A 503 gallon pill of the same reacted product used in Example I was introduced into Well B. The pill was introduced at 10:17 AM and at 10:24 AM, pressuring up of the well was started. At 10:52 AM the final amount of the pill was introduced and Well B was shut in and had a pressure of about 1,300 psi. At 10:54 AM a bullplug was put into the well and the pressure on the well was down to about 1,000 psi. At 11:25 AM the pressure of the still shut in well was about 0 psi. The following day the well was under a vacuum. An operator began pulling on the well with great returns. The returns, after sending the pill into Well B, was greater than 85 bbls of total fluid/day.

Example III

In Example III, a third well (Well C) that began building pressure was treated. Well C was a disposal well for disposing of salt water. It was determined that the pressure in Well C was building due to tank bottoms. A 500 gallon pill of the same reacted product used in Example 1 was introduced into Well C and after about 2 hours, the pressure dropped about 200 psi and additional salt water could again be injected into Well C.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method comprising, removing one or more inorganic mineral scales by contacting the one or more inorganic mineral scales with a composition comprising about 1 wt % to about 80 wt % glyceric acid, about 0.1 wt % to about 10 wt % oxalic acid, about 0.1 wt % to about 3 wt % glycolic acid, and about 1 wt % to about 40 wt % formic acid.

2. The method of claim 1, wherein the one or more inorganic mineral scales is selected from the group consisting of calcium carbonate, calcium sulfate, barium sulfate, sodium chloride, strontium sulfate, strontium carbonate, iron oxide, iron carbonate, iron sulfide, barium-strontium sulfate, magnesium carbonate, magnesium sulfate, and any combination thereof.

3. The method of claim 1, wherein the composition further comprises about 0.1 wt % to about 3 wt % glyceraldehydes.

4. The method of claim 1, wherein the composition further comprises about 0.1 wt % to about 7 wt % hydroxypyruvic acid.

5. The method of claim 1, wherein the composition further comprises about 0.1 wt % to about 3 wt % tartronic acid.

6. The method of claim 1, wherein the composition further comprises about 0.1 wt % to about 40 wt % glycerol.

7. The method of claim 1, wherein the composition further comprises about 0.1 wt % to about 10 wt % methanol.

8. The method of claim 1, wherein the composition further comprises about 1 wt % to about 50 wt % water.

9. The method of claim 1, wherein the composition comprises about 10 wt % to about 80 wt % glyceric acid, about 3 wt % to about 10 wt % oxalic acid, about 0.5 wt % to about 3 wt % glycolic acid, and about 5 wt % to about 40 wt % formic acid, and wherein the composition further comprises about 10 wt % to about 50 wt % water.

10. The method of claim 1, wherein the composition further comprises at least two of:
about 0.1 wt % to about 3 wt % glyceraldehydes,
about 0.1 wt % to about 7 wt % hydroxypyruvic acid,
about 0.1 wt % to about 3 wt % tartronic acid,
about 0.1 wt % to about 40 wt % glycerol, and
about 1 wt % to about 50 wt % water.

11. The method of claim 1, wherein the composition has a flash point of about 30° C. to about 300° C., a freeze point less than about −25° C., and a specific gravity relative to demineralized water of about 1.05 to about 1.5.

12. The method of claim 1, wherein the composition has a pH less than about 3.5, and the method further comprises increasing the pH of the composition to about 6 to about 9 by combining one or more base compounds with the composition prior to contacting the one or more inorganic mineral scales with the composition.

13. A method comprising:
demulsifying an emulsion by mixing the emulsion with a composition;
fracturing a hydrocarbon bearing formation using the composition;
lowering a freeze point of water using the composition; or
using the composition in a wellbore as a drilling fluid or as a component of a drilling fluid, wherein the composition comprises about 1 wt % to about 80 wt % glyceric acid, about 0.1 wt % to about 10 wt % oxalic acid, about 0.1 wt % to about 3 wt % glycolic acid, and about 1 wt % to about 40 wt % formic acid.

14. The method of claim 13, wherein the composition comprises about 10 wt % to about 80 wt % glyceric acid, about 3 wt % to about 10 wt % oxalic acid, about 0.5 wt % to about 3 wt % glycolic acid, about 5 wt % to about 40 wt % formic acid, and wherein the composition further comprises about 1 wt % to about 50 wt % water.

15. The method of claim 13, wherein the composition further comprises at least two of:
about 0.1 wt % to about 3 wt % glyceraldehydes,
about 0.1 wt % to about 7 wt % hydroxypyruvic acid,
about 0.1 wt % to about 3 wt % tartronic acid,
about 0.1 wt % to about 40 wt % glycerol, and
about 1 wt % to about 50 wt % water.

16. A method comprising, contacting a fluid with a composition comprising about 1 wt % to about 80 wt % glyceric acid, about 0.1 wt % to about 10 wt % oxalic acid, about 0.1 wt % to about 3 wt % glycolic acid, and about 1 wt % to about 40 wt % formic acid, wherein by contacting with the fluid, the composition:
(1) removes at least a portion of one or more inorganic mineral scale deposits contained in the fluid,
(2) inhibits a formation of one or more inorganic scales in the fluid,
(3) reduces a freeze point of the fluid,
(4) removes at least a portion of one or more hydrates contained in the fluid,
(5) inhibits a formation of one or more hydrates in the fluid, or
(6) any combination thereof.

17. The method of claim 16, wherein the composition has a pH less than about 3.5, and the method further comprises increasing the pH of the composition to about 6 to about 9 by combining one or more base compounds with the composition prior to contacting the fluid with the composition.

18. The method of claim 16, wherein the composition comprises about 10 wt % to about 80 wt % glyceric acid, about 3 wt % to about 10 wt % oxalic acid, about 0.5 wt % to about 3 wt % glycolic acid, about 5 wt % to about 40 wt % formic acid, and wherein the composition further comprises about 1 wt % to about 50 wt % water.

19. The method of claim 16, wherein the composition further comprises at least two of:
about 0.5 wt % to about 3 wt % glyceraldehydes,
about 1 wt % to about 7 wt % hydroxypyruvic acid,
about 0.5 wt % to about 3 wt % tartronic acid, and
about 5 wt % to about 40 wt % glycerol.

20. The method of claim 16, wherein the composition further comprises about 0.1 wt % to about 3 wt % glyceraldehydes, about 0.1 wt % to about 7 wt % hydroxypyruvic acid, about 0.1 wt % to about 3 wt % tartronic acid, about 0.1 wt % to about 40 wt % glycerol, and about 1 wt % to about 50 wt % water.

* * * * *